United States Patent [19]

Kelsey

[11] 4,007,641
[45] Feb. 15, 1977

[54] MOLTEN METAL SAMPLER WITH VACUUM

[75] Inventor: Edward A. Kelsey, Disley, England

[73] Assignee: Robert C. Collins, Ashippun, Wis.

[22] Filed: Mar. 17, 1975

[21] Appl. No.: 559,046

[30] Foreign Application Priority Data

Mar. 20, 1974 United Kingdom ............. 12363/74

[52] U.S. Cl. ........................... 73/425.6; 73/DIG. 9
[51] Int. Cl.² ........................................ G01N 1/12
[58] Field of Search .............. 73/DIG. 9, 425.4 R, 73/425.6; 164/254, 255

[56] References Cited

UNITED STATES PATENTS

| | | | |
|---|---|---|---|
| 2,515,060 | 7/1950 | Smith | 73/DIG. 9 |
| 2,970,350 | 2/1961 | Feichtinger | 73/DIG. 9 |
| 3,791,220 | 2/1974 | Falk | 73/DIG. 9 |
| 3,915,014 | 10/1975 | Judge et al. | 73/425.6 |

Primary Examiner—S. Clement Swisher
Attorney, Agent, or Firm—Cyril M. Hajewski

[57] ABSTRACT

A molten metal sampler that is provided with a chamber that can be evacuated and is adapted to hold the vacuum until it is to be placed in operation. When the sampler is contacted by the molten metal, a seal holding the vacuum will disintegrate to permit passage of the molten metal into the evacuated chamber.

16 Claims, 8 Drawing Figures

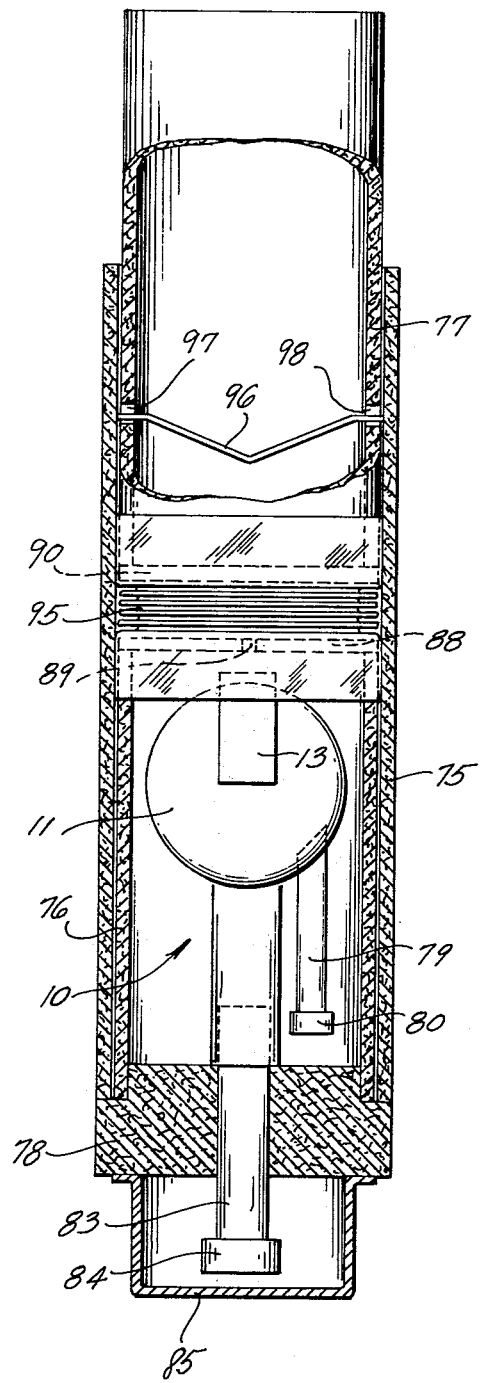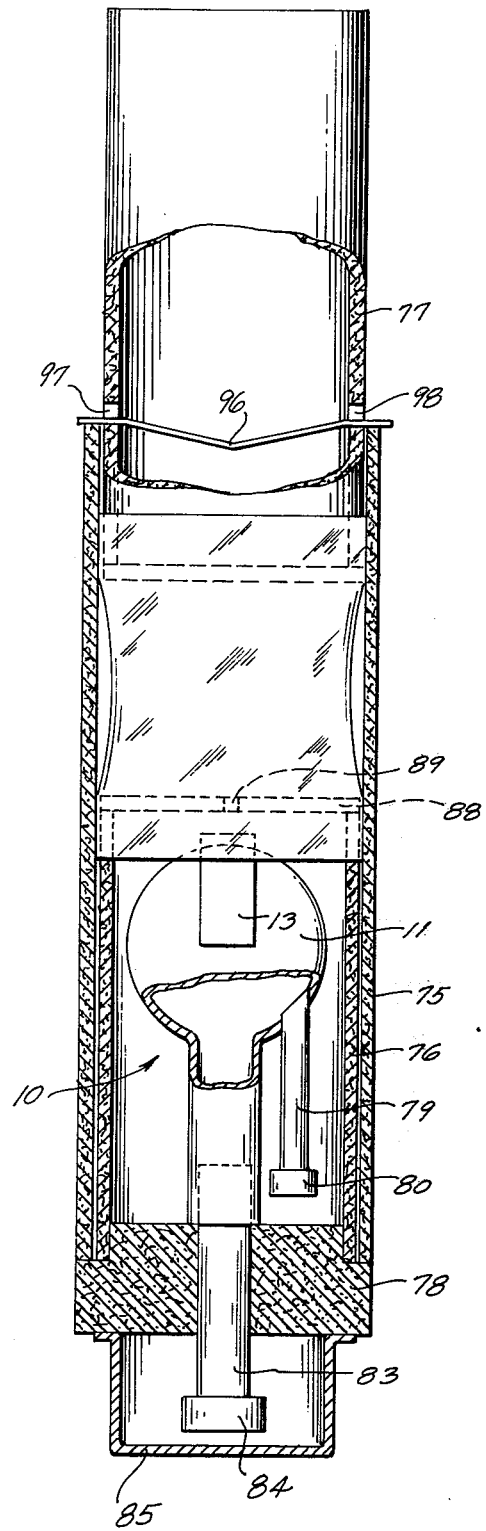

MOLTEN METAL SAMPLER WITH VACUUM

BACKGROUND OF THE INVENTION

In my copending patent application I have disclosed a molten metal sampler formed partially of insulating material and partially of a good conductor of heat to control the cooling of the metal so that a high quality sample of metal will be obtained which can be readily analyzed in the metallurgical laboratory. The molten metal sampler of that invention can be made as a stream sampler or as an immersion sampler. In the former the sampler is especially adapted to be placed in the stream of metal as it flows from one container to another to receive the sample of molten metal. On the other hand, the immersion type sampler is especially adapted to be immersed in a melt of metal to obtain the sample. Thus, the sampler would be immersed in the metal as the latter is in a furnace, ladle or the like and the metal will flow into a sample chamber which is adapted to form and contain the desired sample.

In either case it may be desirable because of the conditions encountered to provide an aid for admitting the molten metal into the sample chamber and such aid is provided in the present invention by evacuating the sample chamber before placing it in use to create a vacuum therein and the chamber is sealed to maintain the vacuum. The seal is formed of a substance that will disintegrate when placed in the molten metal so that the metal will then flow freely into the evacuated chamber.

Such a vacuum assist to the flow of molten metal into the sample chamber is especially desirable when it is difficult or impossible to fully immerse the sampler into the molten metal as may occur when the melt is in a relatively shallow ladle or mold. Moreover, the evacuated chamber will produce a sample which is solid throughout and free of any voids so that a vacuum type sampler may be desirable to use under all conditions where an extremely high quality sample is required.

The advantages of vacuum type molten metal samplers has been previously recognized but they have been constructed in such a manner as to limit the shape of the sample that can be taken or they are inconvenient to operate in the vicinity of molten metal. Thus, vacuum type molten metal samplers are disclosed in U.S. Pat. No. 3,534,614 to Creswell and U.S. Pat. No. 3,369,406 to Lowdermilk et al. In both cases a tube made of glass or other impervious material is evacuated and sealed. The molten metal breaks the seal and flows into the tube. As a result, only a pin type sample can be taken with these constructions because the sample chamber itself is evacuated so that its configuration is strictly limited.

On the other hand, the present invention provides an arrangement in which the sample chamber is placed in an evacuated space so that the sample chamber itself can be of any desired shape. Accordingly the single sample chamber in the evacuated space can be shaped to form the well known paddle shape which produces surfaces that may be readily polished and at the same time can produce the pin for other metallurgical analyses.

The disadvantages of the limited configuration of vacuum type samplers was overcome by the sampler disclosed in U.S. Pat. No. 3,791,220 to Falk et al but it was accomplished by requiring the person taking the sample to operate a pump for reducing the pressure in the sample chamber while the sample is being taken. This requires the person to operate close to the molten metal which may be highly undesirable and virtually impossible under some conditions. This is avoided in the present invention by creating the vacuum before the sampler is placed in the molten metal so that the person taking the sample is not required to operate any mechanism but merely takes the sample in the conventional manner. Yet, the configuration of the sample is not strictly limited as it has been in other prior art vacuum type samplers in which the vacuum is created prior to inserting the sampler into the molten metal.

SUMMARY OF THE INVENTION

According to this invention there is provided an improved vacuum type molten metal sampler in which the receptacle or mold that receives the molten metal to be tested is enclosed in a sealed container from which the atmosphere has been evacuated. The receptacle which is to receive the molten metal is not sealed with respect to the container so that the evacuation of the atmosphere from the container produces a vacuum in the entire container including the molten metal receptacle contained therein.

A filler tube extends from the molten metal receptacle to the exterior of the container and its entrance into the container is sealed so that the atmosphere can be evacuated from the container through the filler tube to create the vacuum. After the vacuum has been created in the container, the open end of the filler tube is sealed to prevent air from leaking back into the container. Thus the molten metal receptacle or mold is disposed in a vacuum when it is assembled at a location which can be completely remote from the metal melt that is to be sampled and it is ready to be placed in operation. The person that is taking the sample merely places the molten metal receptacle including the evacuated container into the metal melt from which the sample is to be taken. The heat of the molten metal will burn off the seal from the filler tube and the vacuum in the sampler will then assist the metal to flow into the receptacle to produce the high quality sample.

The foregoing and other objects of this invention which will become more fully apparent from the following detailed description, may be achieved by means of the exemplifying apparatus depicted in and set forth in this specification in connection with the accompanying drawings.

BRIEF DESCRIPTION OF THE DRAWING

FIG. 7 is a view partly in section and partly in front elevation illustrating a further embodiment of the present invention and which includes means for evacuating the atmosphere from the container in which the molten metal receptacle is contained; and FIG. 8 is another view of the molten metal sampler shown in FIG. 7 after the atmosphere evacuating mechanism has been operated to create the vacuum in the molten metal receptacle and its container.

DESCRIPTION OF THE PREFERRED EMBODIMENTS

Figure 1:
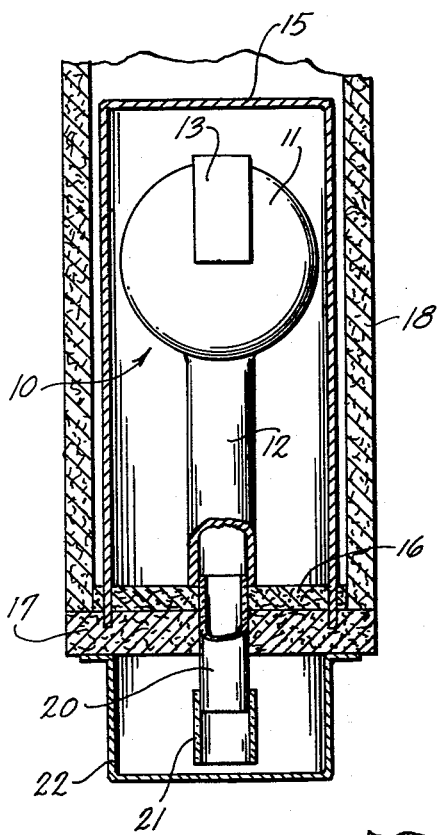
FIG. 1 is a view partly in section and partly in front elevation illustrating a molten metal sampler incorporating features of the present invention.

Reference is now made more particularly to the drawings and specifically to FIG. 1 thereof which illustrates a molten metal sampler incorporating the features of the present invention. The sample of molten metal to be analyzed in the laboratory is received in a metal mold or receptacle generally identified by the reference numeral 10. The mold is the familiar paddle shape having a circular portion 11 and a pin portion 12. Both the circular portion 11 and the pin portion 12 are filled with metal to form two different configurations of samples. The circular portion 11 provides a round metal sample with two flat surfaces that may be readily polished for laboratory analyses. On the other hand, the pin portion 12 yields a sample in the form of a pin which is convenient for other types of laboratory analyses.

Figure 2:
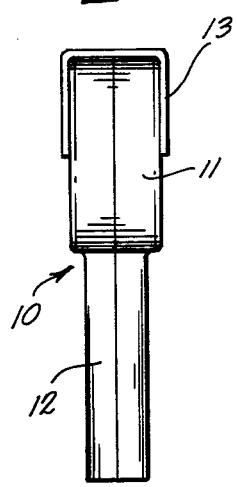
FIG. 2 is a detailed view in side elevation showing the molten metal receptacle that is depicted in FIG. 1.

A side elevational view of the metal mold 10 is shown in FIG. 2 where it is readily apparent that the mold is formed of two identical halves which are held together by a clip 13. The mold 10 is mounted in a metal cannister 15 that is completely closed except for its bottom end which is sealed by a paperboard insert 16 that forms a closure for the cannister 15. In addition, the bottom edge of the cannister 15 extends into a ceramic or ceramic fiber plate 17. A paperboard cylinder or probe 18 extends upwardly from the ceramic fiber plate 17 to completely encompass the cannister 15 for the purpose of protecting it from the heat encountered when the unit is contacted by the molten metal.

A filler tube 20 formed of quartz or ceramic is in communication with the pin portion 12 of the metal mold 12 and extends downwardly therefrom through holes formed in the paperboard insert 16 and the ceramic fiber plate 17. The filler tube 20 is in sealed engagement with the plate 17 and insert 16 so that the interior of the cannister 15 is completely sealed from the atmosphere except for the opening in the filler tube 20.

The present invention provides for creating a vacuum in the metal mold 10 and this is done by evacuating air from the entire interior of the cannister 15. The air is withdrawn from the cannister 15 through the filler tube 20 by any suitable means such as an air pump (not shown). The air will be withdrawn from the metal mold 10 and since it is formed of two halves which are not sealed but only held together by the clip 13, the atmosphere will be evacuated from the entire cannister 15 as well as from the metal mold 10. After a vacuum has been created, the end of the filler tube 20 is sealed and to this end an aluminum sleeve 21 is mounted on the end of the filler tube 20 and is sealed relative to it. In FIG. 1 the sleeve 21 is shown open to render the interior of the cannister accessible for evacuating the air. However, as the vacuum is being created heat is applied to the end of the sleeve 21 and when it becomes pliable it is crimped in the manner shown in FIG. 3 for the sleeve 46 to complete the sealing of the cannister 15.

A further protective aluminum or steel cap 22 is mounted on the end of the unit to enclose the extending end of the filler cap 20 to protect it from damage. When the unit is placed in the molten metal to take the sample, the sealing sleeve 21 and the protective cap 22 will burn away and the molten metal will flow freely into the evacuated metal mold 10 to completely fill the circular portion 11 as well as the pin portion 12 to form samples which will be free of voids and which are excellent for laboratory analyses.

Figure 3:
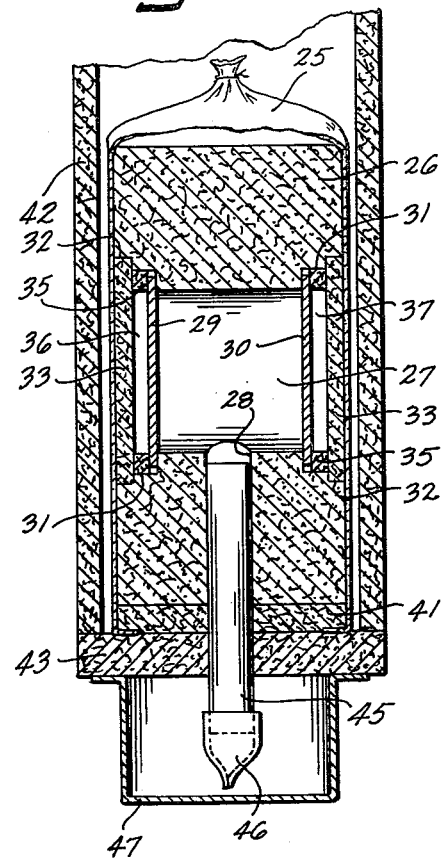
FIG. 3 is a view partly in section and partly in front illustration showing another embodiment of the present invention.

A further embodiment of the present invention is illustrated in FIG. 3 wherein the cannister 15 of FIG. 1 is replaced by a polyethelene plastic bag 25 and the metal mold 10 of the previous embodiment is replaced by a mold formed of a ceramic fiber. The metal mold comprises a ceramic fiber body 26 with a central bore 27 that is in communication with a transverse hole 28 formed in the body 26. One side of the central bore 27 is closed by a circular steel plate 29 and the other end of the bore 27 is closed by a circular steel plate 30. The ends of the bore 27 are provided with a countersink of one diameter 31 to form shoulders for the steel plates 29 and 30 to rest upon. A second counter bore 32 of larger diameter is provided at the extremity of the bore 27 to provide another shoulder for receiving ceramic fiber or paperboard plates 33 which are sealed to the ceramic fiber 26 at each end of the bore 27 to form an air tight closure.

An annular spacer 35 is disposed in the counterbore 31 between the ceramic fiber plate 33 and the steel plate 29 to space the steel plate 29 from the plate 33 and thereby form an air space 36 between them. In like manner a spacer 35 is placed in the counterbore 31 on the opposite side of the bore 27 to space the steel plate 30 from its associated plate 33 to form an air space 37 between them.

The fiber body 26 is enclosed in the polyethylene bag 25 and has its bottom edge sealed between the bottom of the body 26 and the top surface of an insert 41 upon which the body 26 is mounted. The insert 41 supports the body 26 and provides a juncture in which the bottom edge of the polyethylene bag 25 is sealed. A paperboard cylinder 42 encloses the polyethylene bag 25 and its entire contents to protect the unit when it is inserted into the molten metal. A bottom ceramic fiber plate 43 is cemented to the bottom edge of the paperboard cylinder 42 and the insert 41 to complete the seal.

A filler tube 45 extends into the bore 28 of the ceramic fiber body 26 and is sealed to the body as well as to the insert 41 and the ceramic fiber plate 43. An aluminum sleeve 46 is sealed to the end of the filler tube 45 so that it may be heated and crimped to complete the seal in the manner described for the sleeve 21 in FIG. 1. An aluminum or steel cap 47 is mounted on the face of the plate 43 to protect the extending end of the filler tube 45.

In order to create the vacuum within the bore 27, the atmosphere is evacuated therefrom through the filler tube 45 by any suitable means, such as an air pump, and as the air is being evacuated the sleeve 46 is heated and crimped to complete the seal. The aluminum or steel cap 47 is then placed on the end of the unit to protect the extending end of the filler tube 45. When the unit is placed in the molten metal to take the sample, the sleeve 46 and cap 47 will burn away to permit the molten metal to flow freely through the filler tube 45 into the chamber formed by the bore 27 to form the metal sample.

The steel plates 29 and 30 are not air tight relative to the body 26 and it has been found that if there are any gases in the molten metal they will escape therefrom around the metal plates 29 and 30 and enter the spaces 36 and 37 which have likewise been evacuated with the bore 27. The resulting sample in the bore 27 as well as the pin in the bore 28, will therefore be entirely free of voids and provide excellent solid samples for laboratory analyses.

Figure 4:
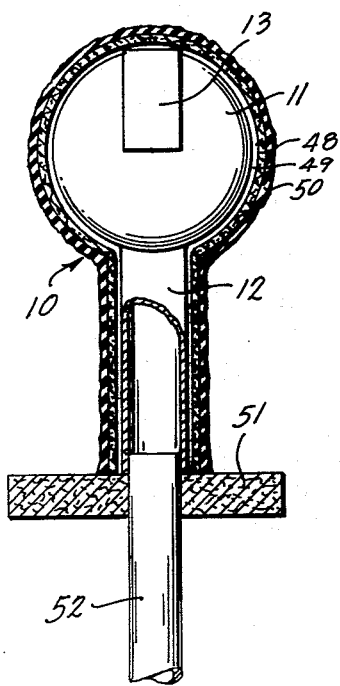
FIG. 4 is a view partly in section and partly in front elevation depicting another embodiment of the present invention.

The embodiment illustrated in FIG. 4 is of a relatively simple construction in which the same metal mold 10 that is shown in FIGS. 1 and 2 is employed. As previously described, the mold is formed of two halves held together by a clip 13.

The entire metal mold is encased in a paper mache enclosure 48 which is spaced from the mold 10 to form a space 49 between the metal mold 10 and the paper mache enclosure 48. This space is advantageous for providing a space into which the gases may escape from the molten metal as it enters the mold 10. If the space is not available for receiving the gases they will remain in the metal and form voids that detract from the quality of the sample.

The exterior of the paper mache enclosure 48 is coated with a sealant 50 to render it airtight. An excellent sealant for this purpose is an ablative material such as Dow Corning No. 93-904 ablative material which can be coated onto the exterior of the metal mold 10 and will solidify into a rubbery material which effectively seals the metal mold 10.

One of the outstanding advantages of such ablative material is that it constitutes an excellent seal to enable a vacuum to be created within the paper mache enclosure and the interior of the metal mold 10. However, once the molten metal sampler is in contact with the molten metal to subject the ablative material to heat for a short period of time it disintegrates and disappears so that it in no way interferes with the removal of the metal from the sampler. Thus, the ablative provides the sealing desired and maintains such sealing when the sampler is initially placed in the molten metal. However, after it is subjected to the high temperatures for a short period of time it disappears and the paper mache enclosure 48 will burn away so that the metal sample taken may be then very readily removed from the metal mold 10.

The mold 10 and paper mache enclosure shown in FIG. 4 are mounted on a paperboard plate 51 and the sealant material 50 seals the juncture of the metal mold 10 and the paper mache enclosure 48 with the paperboard plate 51. A filler tube 52 extends through the paperboard plate 51 and into the interior of the metal mold 10. A suitable sealant is provided to seal the juncture of the filler tube 52 with the plate 51 and metal mold 10. The atmosphere from the metal mold 10 is evacuated through the filler tube 52 which is then sealed to maintain the vacuum therein in the manner previously described for the other embodiments. When the unit is inserted into the molten metal the seal on the filler tube 52 will disappear and the metal will flow freely into the metal mold 10. Continued subjection to the heat of the molten metal will cause the ablative material 50 to disappear and the paper mache enclosure 48 to burn away so that when the unit is withdrawn from the metal the metal mold 10 is completely free of a sealant.

The paper mache enclosure 48 is shown in FIG. 4 to create the air space 49 to provide for the escape of the gases from the molten metal. However, if the gases are not a problem, the paper mache enclosure can be omitted and the sealing material 50 would then be coated directly on the metal mold 10.

Figure 5:
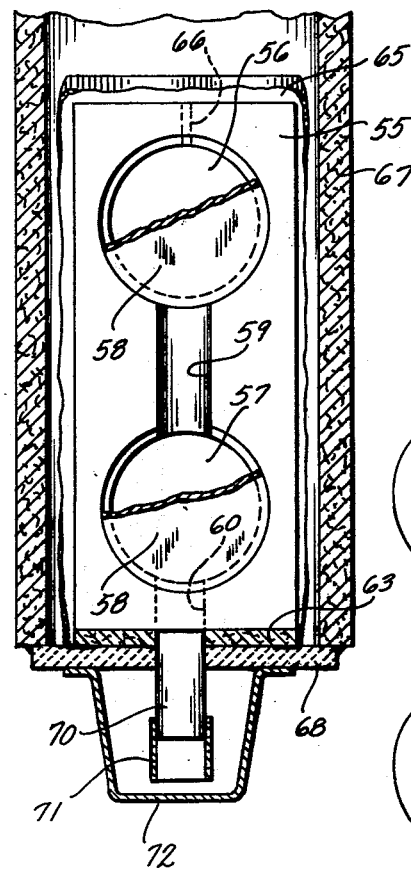
FIG. 5 is a view partly in section and partly in front elevation illustrating a further embodiment of the present invention.
Figure 6:
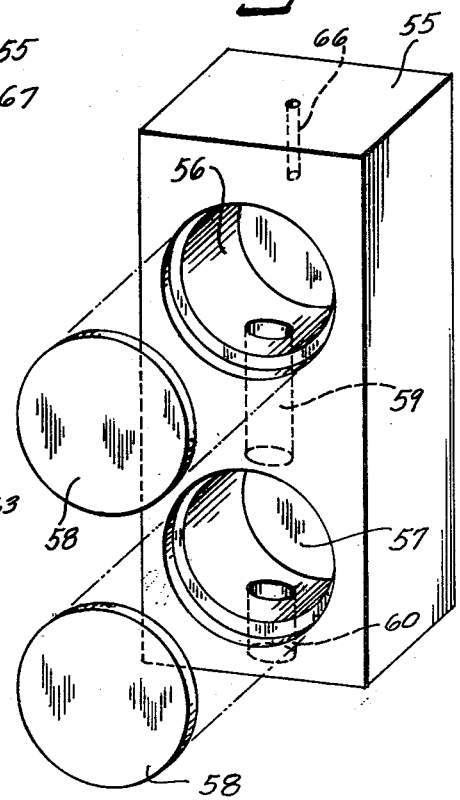
FIG. 6 is a perspective exploded detailed view showing the molten metal receptacle that is depicted in FIG. 5.

The embodiment illustrated in FIGS. 5 and 6 is similar to that shown in FIG. 3 except that a modified mold structure is provided for receiving the molten metal. The mold is formed of a mineral fiber and comprises a mineral fiber body 55 having two bores 56 and 57, both of which are closed by a steel plate 58. In FIG. 6, the steel plates 58 are shown removed from the body 55 to open the bores 56 and 57. However, when the steel plates 58 are placed to close the openings 56 and 57 as shown in FIG. 5, they form a chamber with the bores 56 and 57 for receiving the molten metal. To this end, the two bores 56 and 57 are connected by a transverse hole 59. A filler hole 60 extends from the bore 57 through the exterior of the body 55 to provide a passage for the molten metal to enter the chambers formed by the bores 56 and 57.

The body 55 rests upon a ceramic or ceramic fiber plate 63 and is enclosed in a polyethylene bag 65 which encloses the entire body 55 and is sealed between the bottom of the ceramic fiber plate 63 and the top face of a ceramic plate 68 so that a vacuum may be drawn in the chambers formed by the bores 56 and 57. To assist in forming such vacuum, the bore 56 is provided with a small vent 66 which is small enough to prevent the flow of molten metal through it but will readily admit the passage of air.

The entire unit is enclosed in a paperboard cylinder 67 that has its bottom end closed by a ceramic plate 68. A filler tube 70 extends through suitable holes formed in the plate 68 and mineral fiber plate 63 into communication with the filler hole 60 of the body 55. The filler tube 70 is sealed at its juncture with the plates 63 and 68 so that the atmosphere from the fiber mold body 55 can be evacuated through the filler tube 70. The filler tube 70 is provided with an aluminum sleeve 71 that is sealed to the filler tube 70. As the vacuum is being created within the polyethylene bag 65, the end of the aluminum 71 is heated and crimped in the manner previously described for the other embodiments. In addition, an aluminum or steel cap 72 is mounted on the face of the ceramic plate 68 and covers the entire filler tube 70 and its associated aluminum sleeve 71. As previously described for the other embodiments, the cap 72 and sleeve 71 will disintegrate when placed in the molten metal to admit the flow of metal through the filler tube 70 into the bores 56 and 57. The hole 59 will likewise fill up with molten metal to form a pin sample for laboratory analyses while the samples in the bores 56 and 57 are especially well adapted for polishing. Since the vacuum was created in the bores 56 and 57 as well as the hole 59, the metal therein will flow freely and will be free of voids.

The embodiment illustrated in FIGS. 7 and 8 is an arrangement in which the vacuum is created in the metal mold just prior to the time the sample of molten metal is taken. It includes an outer paperboard cylinder 75 in which are contained a paperboard cylinder 76 and another paperboard cylinder 77. The bottom of the inner paperboard cylinder 76 is closed by a mineral fiber plug 78 and mounted upon the plug 78 is the metal mold 10 described in connection with FIGS. 1 and 2. As previously described, the metal mold 10 is formed of the two halves held together by a clip 13. The mold 10 shown in FIGS. 7 and 8 is also provided with a tube 79 in communication with the circular portion of the mold 10, the tube 79 being closed by an end cap 80. The tube 79 is provided for obtaining a pin shaped sample for test purposes. A filler tube 83 extends through the plug 78 into communication with the interior of the metal mold 10 so that the metal to be tested can flow through the filler tube 83 into the metal mold 10. The end of the filler tube 83 is sealed by an aluminum cap 84 and another aluminum or steel cap 85 is mounted on the face of the plug 78 to protect the entire filler tube 83 extending beyond the plug 78. The top of the paperboard cylinder 76 is provided with a cover 88 and a hole 89 is formed in the cover 88 as shown in FIGS. 7 and 8.

The cylinder 77 is slidably contained within the cylinder 75 for axial movement relative to the cylinder 76. The cylinder 77 has its bottom end closed by a plate 90 and is connected with the cylinder 76 by a flexible sleeve 95 formed of an impervious material such as polyethylene plastic or latex. The sleeve 95 is air-tight and is sealed to the bottom end of the upper cylinder 77 as well as to the upper end of the lower cylinder 76. In FIG. 7, the cylinder 77 is shown in its lower position with the sleeve 95 collapsed. When the sample of molten metal is to be taken, the cylinder 77 is raised to the position shown in FIG. 8 which causes it to extend the sleeve 95 and thereby evacuate the atmosphere from the interior of the cylinder 76 through the hole 89. The unit is then immersed in the molten metal which will cause the caps 84 and 85 to melt away and open the filler tube 83 for receiving the molten metal. The vacuum created in the cylinder 76 will cause the molten metal to readily flow through the filler tube 83 into the metal mold 10 and its associated tube 79.

A spring rod 96 is disposed in the interior of the cylinder 77 with one end of the spring rod 96 being disposed in a hole 97 formed through the wall of the cylinder 77 and through another hole 98 formed in the wall of the cylinder 77 diametrically opposite from the location of the hole 97. When the cylinder 77 is moved outwardly to extend the flexible sleeve 95 the holes 97 and 98 will be located above the top edge of the outer cylinder 75 to enable the spring 96 to expand outwardly over the top edge of the cylinder 75. This will prevent the cylinder 77 from moving downwardly so that the flexible sleeve 95 will be locked in its extended position to maintain the vacuum within the metal mold 10.

From the foregoing detailed description of the illustrative embodiments of the invention set forth herein, it will be apparent that there has been provided an improved vacuum type molten metal sampler that especially adapted to assist the flow of metal into the mold that receives the sample but yet does not limit the configuration of the mold so that the conventional molds such as the well known paddle type mold may be employed for receiving the samples to be taken. The conventional configuration of the molds are employed for receiving the sample but the samples are of improved quality because of the fact that the metal enters an evacuated chamber.

Although the illustrative embodiments of the invention have been described in considerable detail for the purpose of disclosing practical operative arrangements by means of which the invention may be practised advantageously, it is to be understood that the particular molten metal samplers illustrated and described are intended to be illustrative only and that the various novel characteristics of the invention may be incorporated in other structural forms without departing from the spirit and scope of the invention as defined in the subjoined claims.

The principles of this invention having now been fully explained in connection with the foregoing description, I hereby claim as my invention:

1. In a molten metal sampler; a container adapted to be mounted at the end of a probe; a mold in said container for receiving the sample of molten metal; means permitting the flow of air between the interior of said mold and said container but preventing the flow of molten metal out of said mold; air tight sealing means for sealing said container so that the atmosphere can be evacuated from said container as well as from the mold in said container and the vacuum can be maintained therein; and filler means for admitting molten metal into said mold while the mold is in said container and while the vacuum is maintained in said container for assisting the flow of molten metal into said mold.

2. A molten metal sampler according to claim 1 wherein said container is a metal cannister that contains said mold.

3. A molten metal sampler according to claim 1 wherein said container is a flexible material that is impervious to air and is sealingly engaged about said mold.

4. A molten metal sampler according to claim 1 wherein said container is a coating on the surface of said mold, said coating being impervious to air to seal said mold so that the atmosphere can be evacuated from its interior.

5. A molten metal sampler according to claim 1 wherein said container is a paper mache enclosure completely surrounding said mold; and including a coating on the outer surface of said paper mache enclosure to render it airtight so that the air can be evacuated from said mold.

6. A molten metal sampler according to claim 5 wherein said paper mache enclosure is spaced from the outer surface of said mold to create a space into which the gases in the molten metal can escape.

7. A molten metal sampler according to claim 1 wherein said mold is formed of two identical halves; and a clip holds the two halves together in said container.

8. A molten metal sampler according to claim 7 wherein said mold includes a circular portion for forming a flat circular metal sample and a pin portion for forming a pin shaped sample of the metal.

9. A molten metal sampler according to claim 1 wherein said mold includes a chamber for receiving the metal to be sampled, said mold having some walls formed of an insulating material and some walls formed of a good conductor of heat so that the cooling of the metal sample can be accurately controlled.

10. A molten metal sampler according to claim 1 wherein said mold comprises a mineral fiber body having an aperture and a filler hole extending from the aperture to the exterior of said body for admitting the molten metal into the aperture, and metal plates closing the aperture to form a chamber for receiving the molten metal to be sampled.

11. A molten metal sampler according to claim 10 wherein said metal plates are not sealed to said body so that gases in the molten metal received in the chamber can escape past said plates.

12. A molten metal sampler according to claim 11 including two exterior plates with each plate closing one end of the aperture, and one of said metal plates is spaced interiorly of each of said exterior plates so that a space is formed between each metal plate and its associated exterior plate, such space providing room for the gases to escape from the molten metal entering the chamber, the gases flowing past said metal plates into the spaces.

13. A molten metal sampler according to claim 1 including evacuating means mounted on said container and operable to evacuate the atmosphere from said container for forming the vacuum therein.

14. A molten metal sampler according to claim 13 wherein said evacuating means comprises an actuator movable relative to said container, an impervious sleeve having two open ends with one end being sealingly connected to said actuator and its other end sealingly connected to said container, said actuator being moved away from said container to extend said sleeve from a collapsed condition to an extended condition for evacuating the atmosphere from said container.

15. In a molten metal sampler; a support; a container fixedly supported in said cylinder; a mold in said container for receiving the metal that is to be sampled; a filler tube in communication with said mold and extending through said container to form a passage for the molten metal to flow into said mold; a heat sensitive seal on said filler tube which seals the tube at ambient temperatures but melts when subjected to the heat of the molten metal to admit the flow of molten metal through said filler tube; and evacuating means carried by said support operable to create a vacuum in said container for evacuating the atmosphere from said container and thereby the mold in said container for assisting the flow of molten into said mold and producing a high quality sample.

16. A molten metal sampler according to claim 15 wherein said evacuating means comprises an actuator slidably supported by said support; and an impervious sleeve having two open ends with one end being in sealed engagement with said actuator and the other end being in sealed engagement with said container, said sleeve being movable by said actuator from a collapsed condition to an extended condition; and said container is provided with an opening in communication with the interior of said sleeve so that when said actuator moves said sleeve from the collapsed condition to the extended position it operates to evacuate the atmosphere from said container and the mold contained therein.

* * * * *